United States Patent
Denoth et al.

(10) Patent No.: US 7,632,263 B2
(45) Date of Patent: Dec. 15, 2009

(54) CONNECTING DEVICE FOR PERCUTANEOUSLY IMPLANTED PORT SYSTEM

(75) Inventors: Patrik Denoth, Aarwangen (CH); Sandro Niederhäuser, Bleienbach (CH); Astrid Valiquer, Villar-Ste-Croix (CH)

(73) Assignee: Disetronic Licensing AG, Burgdorf (CH)

( * ) Notice: Subject to any disclaimer, the term of this patent is extended or adjusted under 35 U.S.C. 154(b) by 669 days.

(21) Appl. No.: 10/789,365

(22) Filed: Feb. 27, 2004

(65) Prior Publication Data

US 2004/0249361 A1 Dec. 9, 2004

Related U.S. Application Data

(63) Continuation of application No. PCT/CH02/00462, filed on Aug. 23, 2002.

(30) Foreign Application Priority Data

| Aug. 31, 2001 | (DE) | 101 42 637 |
| Sep. 6, 2001 | (DE) | 201 14 795 U |
| Oct. 29, 2001 | (DE) | 101 53 341 |

(51) Int. Cl.
*A61M 25/00* (2006.01)

(52) U.S. Cl. .......... 604/523; 604/890.1; 604/891.1; 604/93.01; 604/175; 604/288.01; 604/288.02; 604/288.04; 604/533; 604/534; 604/535

(58) Field of Classification Search ... 604/890.1–891.1, 604/523, 93.01, 288.01–288.02, 288.04, 604/175, 905, 533–535
See application file for complete search history.

(56) References Cited

U.S. PATENT DOCUMENTS

| 4,488,877 | A | * | 12/1984 | Klein et al. | 604/175 |
| 4,645,494 | A | * | 2/1987 | Lee et al. | 604/175 |
| 5,098,397 | A | * | 3/1992 | Svensson et al. | 604/175 |
| 5,810,792 | A | * | 9/1998 | Fangrow et al. | 604/533 |
| 6,007,516 | A | * | 12/1999 | Burbank et al. | 604/288.03 |
| 6,261,266 | B1 | | 7/2001 | Jepson et al. | |
| 6,270,475 | B1 | * | 8/2001 | Bestetti et al. | 604/93.01 |

FOREIGN PATENT DOCUMENTS

WO   WO 99/34754   7/1999

* cited by examiner

*Primary Examiner*—Nicholas D Lucchesi
*Assistant Examiner*—Quynh-Nhu H Vu
(74) *Attorney, Agent, or Firm*—Dorsey & Whitney LLP

(57) ABSTRACT

A port system including an implantable first fluid guiding system, an external second fluid guiding system with a connecting head at one end, a percutaneously implantable port for establishing a fluid connection between the fluid guiding systems, the port including a port casing which forms a first connecting element, and a connecting device which includes a second connecting element, wherein the connecting head is fastened to the port casing by a releasable, engagement of the connecting elements, several embodiments of which connecting elements are encompassed.

18 Claims, 5 Drawing Sheets

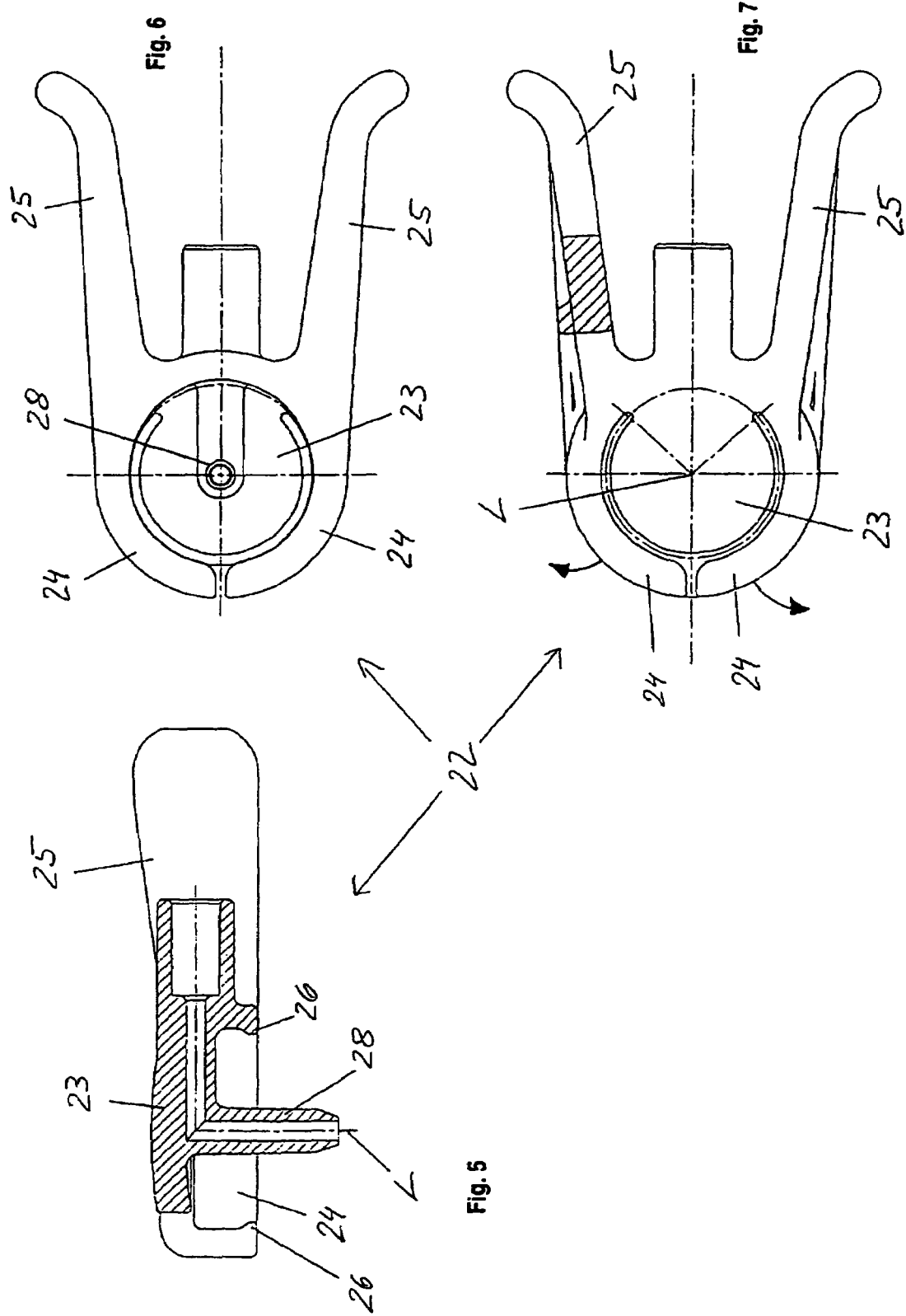

CONNECTING DEVICE FOR PERCUTANEOUSLY IMPLANTED PORT SYSTEM

CROSS-REFERENCE TO RELATED APPLICATION(S)

This application is a continuation of International Application No. PCT/CH02/00462, filed on Aug. 23, 2002, which claims priority to German Application No. 101 42 637.2, filed on Aug. 31, 2001, German Application No. 201 14 795.5, filed on Sep. 6, 2001, and German Application No. 101 53 341.1, filed Oct. 29, 2001, the contents of which are incorporated herein in their entirety by reference.

BACKGROUND

The present invention relates to medical technology, including delivery of medicinal substances and devices and systems for such delivery, including percutaneously implanted or implantable ports. More particularly, relates to implantable ports and connectors or connecting structures serving to mechanically connect an external fluid guiding system to the port. The invention further relates to a port system which includes a percutaneously implantable port and a connecting device as components. In some embodiments, the present invention is preferably employed in the areas of infusion, dialysis, perfusion and in applications or uses serving measuring purposes.

In medicinal technology, in particular in human medicine, fluid guiding systems—which for example comprise or are formed by catheters—have to be connected to each other in a sealed and sterile fashion. The connection is particularly critical in the case of body access devices, so-called ports, which are permanently implanted in a biological tissue, in particular in the human body. For a long time, subcutaneous—i.e. completely implantable—ports have been employed which are used for long-term and intermittent medicine applications. Complications of subcutaneously implanted ports are infection, catheter occlusions and migrations. In addition, the port systems in question only allow a medicine to be continuously dispensed—such as is necessary when continuously dispensing morphines in the treatment of chronic pain—in very difficult circumstances.

The port system DiaPort® developed by the Applicant represents a substantial innovation in this regard. The DiaPort® system is provided for continuous intraperitoneal and intraumbilical-venous administration of insulin. As opposed to the subcutaneous systems, the port of the DiaPort® system is not completely, but rather percutaneously implanted. A small part of the port protrudes outwards beyond the surface of the skin and is visible from without, i.e. externally, and accessible for a connection to an external fluid guiding system. The DiaPort® system is described in EP 0 867 196, EP 0 867 197 and EP 0 867 198.

One end of the external fluid guiding system of the DiaPort® system comprises a connecting cannula which is spherically swelled at its front, free end. When connected, i.e. when the external fluid guiding system is connected to the implanted fluid guiding system, the connecting cannula protrudes into a casing of the port and through a sealing membrane accommodated in the port casing. The spherically swelled end of the connecting cannula prevents the membrane from being damaged by the penetrating connecting cannula. Since the membrane consists of an elastic material which elastically closes onto the connecting cannula in a seal behind the swelled end of the cannula, the spherical swell simultaneously also forms a connecting device which fastens the external fluid guiding system to the port, namely to its membrane.

SUMMARY

It is an object of the invention to improve the mechanical connection between a percutaneously implanted or implantable port and an external fluid guiding system. It should be possible to establish the connection simply and to release it again, and to ensure that the connection between the parts is stable.

In one embodiment, the present invention comprises a port system including an implantable first fluid guiding system, an external second fluid guiding system with a connecting head at one end, a percutaneously implantable port for establishing a fluid connection between the fluid guiding systems, the port comprising a port casing which forms a first connecting element, and a connecting device which includes a second connecting element, wherein the connecting head is fastened to the port casing by a releasable engagement of the connecting elements.

A port system that the present invention may relate to comprises an implantable first fluid guiding system, an external second guiding system, a percutaneously implantable port and a connecting device. When implanted, the percutaneous port connects the two fluid guiding systems fluidically and mechanically. A casing of the port, which protrudes via an upper side out from the tissue when implanted, forms a first connecting element. The connecting device forms a second connecting element. One end of the second fluid guiding system comprises a connecting head which connects and/or fastens the second fluid guiding system to the port casing in a fastening engagement in which the connecting elements are connected to each other. The fastening engagement of the connecting elements can be released, preferably repeatedly established and released.

The port system can be used, for example, within the framework of a venous treatment. For example it may be used in: oncology, the treatment of AIDS, pain, mucoviscidosis, blood coagulation deficiencies, asthma, spasticity, osteomyelitis, for parenteral feeding, in diabetes therapy for administering insulin, and other treatments.

In accordance with the present invention, the fastening engagement is a positive and frictional lock. The fastening is such that the connecting elements and therefore the port casing and the connecting head are pressed against each other with a pressing force. Since the connecting head is held on the port casing, and not on a membrane accommodated in the casing, by the fastening engagement, the connection in accordance with the invention is very stable. No mechanical forces or at most negligible mechanical forces act between the membrane which sterilely seals the port casing from the outside and a connecting element—in some embodiments, preferably a connecting cannula—of the connecting head which protrudes through the membrane. In as far as external forces act at all, they are absorbed by the port casing. By relieving external forces, it is further possible to ensure that the connecting cannula of the connecting head assumes a position in the port casing which is always defined and that the flow of fluid at a transition between the two fluid guiding systems is not disrupted by external forces.

In some embodiments, the connecting elements are preferably formed such that the fastening engagement is established by pushing the connecting head against the port casing. For purposes of description, an axis along which this pushing occurs is referred to as the connecting axis. In some embodiments, it preferably coincides with a longitudinal axis of a connecting cannula which projects from the connecting head. Preferably, the connecting head is connected by the fastening engagement to the port casing such that it cannot be axially moved with respect to the connecting axis.

In some embodiments, the fastening engagement is preferably a latching engagement. One of the connecting elements forms a latching protrusion and the other a latching projection which grips behind the latching protrusion when connected. During latching, the latching projection slides over the latching protrusion and is preferably already moved transverse to the direction of the sliding movement, counter to a restoring elasticity force, by the sliding movement alone. The restoring elasticity force causes the latching projection to again advance transverse to the direction of the sliding movement in the course of the subsequent sliding movement, up to a latching collar formed behind the latching protrusion. The direction of the sliding movement preferably points generally perpendicularly to an upper side of the port casing, i.e. it also preferably points generally perpendicularly to the surface of the skin when the port is implanted. In the way, the forces acting transverse to the surface of the skin during connecting are kept to a minimum.

In a preferred embodiment, the connecting head—in the fastening engagement of the connecting elements relative to the port casing—can be rotated about an axis which points generally perpendicularly to the upper side of the port casing and preferably coincides with the connecting axis. When the port is implanted, the connecting head can thus be rotated relative to the port casing about an axis generally perpendicular to the surface of the skin, such that forces acting on the connecting head at a tangent to the surface of the skin, caused for example by movements of the body, are not introduced into the port casing. In one preferred latching engagement, the latching projection—when rotated—slides along the latching collar formed by the latching protrusion. The axis of rotation coincides with the longitudinal axis of the connecting cannula.

In one preferred embodiment, the connecting device forms a pair of pincers. The second connecting element forms a jowl of said pincers and may therefore also be referred to herein as a connecting jowl. The connecting device comprises a base body from which the connecting jowl can be elastically spread or splayed in order to establish the fastening engagement and release it again. Although the base body itself can form a counter jowl of the pincers, in some embodiments, the connecting device more preferably comprises, in addition to the second connecting element and the base body, another connecting jowl which can likewise be elastically splayed from the base body. In some embodiments, the two connecting jowls in this case exhibit the same shape and are symmetrical with respect to an axis of symmetry which extends transverse to the connecting axis.

In some embodiments, the at least one connecting jowl is extended beyond a splaying axis in order to form a grip element. Splaying axis refers to the axis about which the connecting jowl performs its splaying movement. The other connecting jowl, if one is provided, is similarly extended beyond its splaying axis, to form a grip element. The at least one grip element and, in some embodiments, preferably both grip elements, serve(s) to release the fastening engagement of the connecting elements. For while, in some embodiments, the fastening engagement is preferably established automatically by pressing the connecting head against the upper side of the port casing, releasing the fastening engagement can be at least facilitated by operating the grip elements. By operating the at least one grip element, the connecting elements are moved out of their fastening engagement such that the connecting head is released from the port casing without exerting tensile forces, and can be removed.

In one preferred development or embodiment of the present invention, two grip elements that can be pressed towards each other about the splaying axis in order to release the connection are bent towards each other at their ends. In a preferred embodiment, they form a closed arc, such that an eye-shaped grip part arises. Forming the grip part in the shape of an eye, with a round outer contour—elliptically for example—has the advantage that the connecting device can not get caught in items of clothing, such that it is possible to even more reliably rule out the possibility of undesirable forces being introduced into the port casing via the connecting device.

While the splaying axis of the at least one connecting jowl can in principle point transverse to the connecting axis, in some preferred embodiments it points in the same direction as the connecting axis.

In some embodiments, the connecting device is preferably formed by a single body. In principle, however, the second connecting element could be produced as a separate part and movably supported against a spring element on a base body of the connecting device. If the connecting device comprises a number of second connecting elements, produced as separate parts, this would apply to each of said connecting elements.

The connecting head and the connecting device can each be produced in one piece but separately from each other, and then connected to each other. In other preferred embodiments, the connecting head is produced together with the connecting device in one piece.

In some embodiments, if a pair of pincers forms the connecting device, such a connecting device can form a part separate from the connecting head. The connecting head would be moved, relative to the port casing, to a position suitable for connecting, and the separate connecting device then attached such that the connecting head is connected to the port casing in a positive and frictional lock by being pressed onto the port casing. Substantially simpler handling results, however, if the connecting device is connected to the connecting head from the start, such that these two parts need not be connected to each other only when the connecting head and the port casing are connected. In some preferred embodiments, the connecting head directly forms the connecting device.

BRIEF DESCRIPTION OF THE DRAWINGS

FIG. 5 is a sectional representation of a connecting head of the port system;

FIG. 6 is a view of the underside of the connecting head;

FIG. 7 is a view of the upper side of the connecting head.

DETAILED DESCRIPTION

Figure 1:
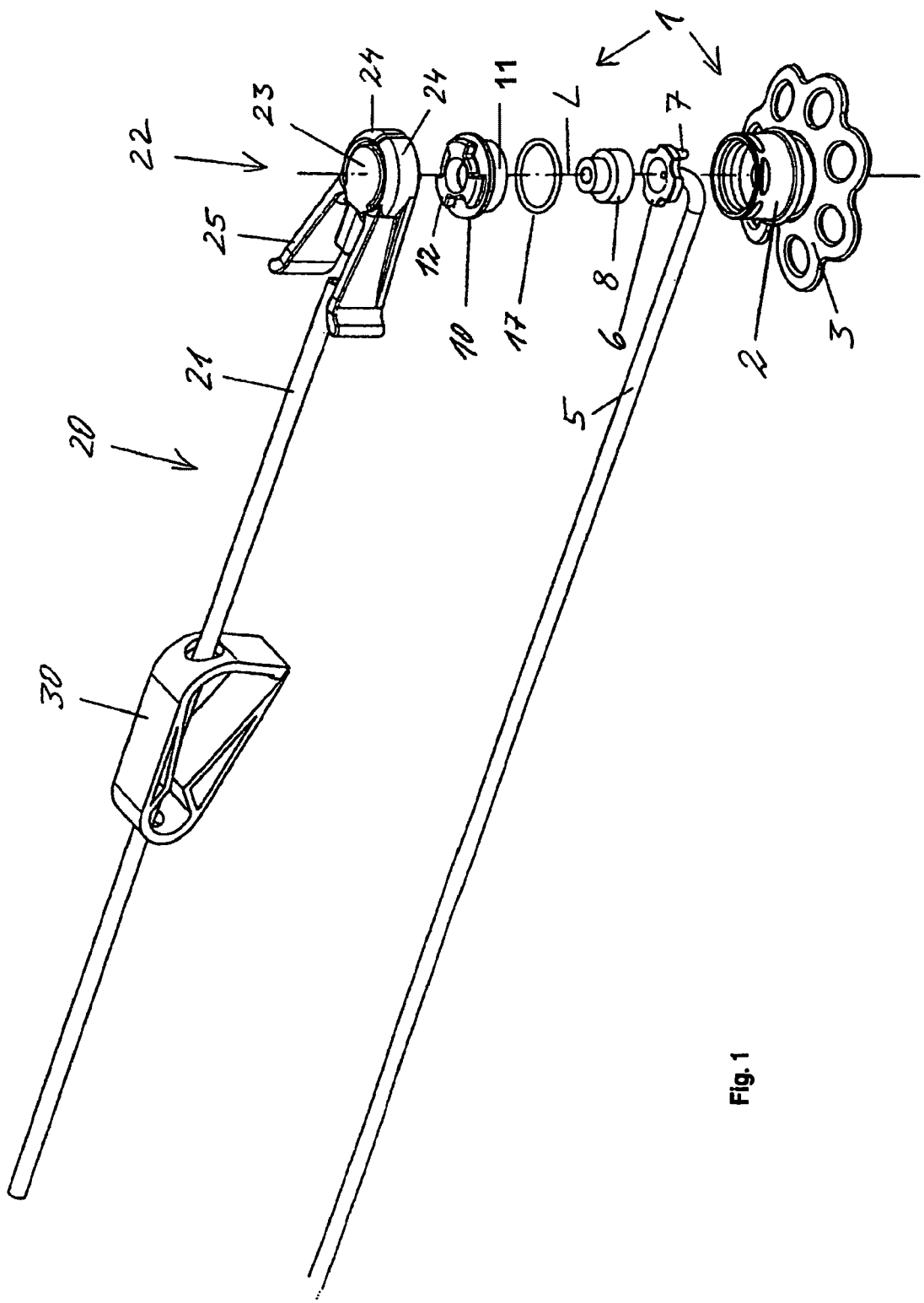
FIG. 1 depicts components of one embodiment of a port system in accordance with the present invention, each in an individual representation.

FIG. 1 shows the components of an exemplary port system in accordance with the present invention. The port system comprises an implantable first fluid guiding system formed by a catheter 5 and a disc-shaped supporting body 6, a percutaneous port, and an external second fluid guiding system 20. The percutaneous port is provided for percutaneous implantation and comprises a hollow-cylindrical main casing 2 and an anchoring body 3. On an underside of the main casing 2, the anchoring body 3 projects radially and peripherally sloping from the main casing 2 towards its outer rim. It serves to anchor the percutaneous port beneath the skin. The percutaneous port further comprises a membrane 8, a sleeve-shaped membrane casing 10 and an O-ring 17. To form the percutaneous port, the membrane 8 is inserted into the membrane casing 10. The membrane casing 10, with the inserted membrane 8, is inserted into the main casing 2 and fastened, for example by means of any appropriate screw connection. When connected, the main casing 2 and the membrane casing 10 jointly form the port casing. Before the membrane casing 10 is inserted, the catheter 5 is pushed through a casing opening on the underside of the main casing 2 until the supporting body 6 is sat on a base of the main casing 2.

In FIG. 1, the components of the percutaneous port and the supporting body 6 are shown along a common longitudinal axis L. The centricity with respect to the common longitudinal axis L is maintained when assembled. In particular, the longitudinal axis L extends through the casing opening in the base of the main casing 2, through a centred opening in the supporting body 6, through a passage through the membrane 8 and through the membrane casing 10.

In one embodiment, the catheter 5 and the supporting body 6 are connected to each other by an arc-shaped prefabricated connector piece. The catheter 5 may be continuously extruded from a bio-compatible plastic and cut to length. In some embodiments, the supporting body 6 is moulded as one piece together with the curved connector piece in an injection-moulding process, likewise from a bio-compatible plastic material. The catheter 5 is then joined to the free end of the curved connector piece and connected in a material lock. In some preferred embodiments, the connector piece together with the supporting body 6 is injection-moulded onto the end of the catheter 5. In a second embodiment, in which the catheter 5 is formed, for example, from PUR, the catheter 5 is continuously extruded and cut to length. The supporting body 6 is again injection-moulded as one piece without the connector piece, and injection-moulded in the injection-moulding process onto an end of the catheter which has been cut to length. The catheter 5 is then thermally remoulded in its section connected to the supporting body 6, such that an arc-shaped section is obtained, connected to the supporting body 6.

The external fluid guiding system, as a third component of the port system, is referred to herein as a whole by the reference numeral 20. It comprises a catheter 21, which is connected at one end to a connecting head 22. The connecting head 22 serves to establish the fluid connection between the catheter 21 and the implantable or implanted catheter 5 and to fasten the external catheter 21 to the percutaneous port. For fastening, the connecting head 22 forms a connecting device in the shape of a pair of splaying pincers comprising two connecting elements 24 formed by pincer jowls and correspondingly two grip elements 25, each formed by a pincer arm. A splaying axis of the pincers points parallel to the longitudinal axis L. The splaying axis extends, at a distance from the longitudinal axis L, through a region of the connecting head 22 level with the transition from the connecting elements 24 to their respective grip element 25. In order to establish the fluid connection to the implantable or implanted fluid guiding system and the mechanical connection to the port, the connecting head 22 is pressed against the upper side of the port along the longitudinal axis L and thus latched to the port. The longitudinal axis L forms a connecting axis along which the connecting head 22 moved relative to the port during connecting.

Furthermore, a pinching clamp 30 is pushed onto the catheter 21. The pinching clamp 30 forms an upper clamp limb, fixed with respect to the catheter 21, and a lower clamp limb which can be pressed against the upper clamp limb. The lower clamp limb is held by a releasable latching engagement in the position in which it is against the upper clamp limb. In the latching engagement, the catheter 21 is pinched between the two clamp limbs, such that the fluid supply or discharge through the catheter 21 is interrupted. In FIG. 1, the two clamp limbs are not pressed against each other.

Figure 2:
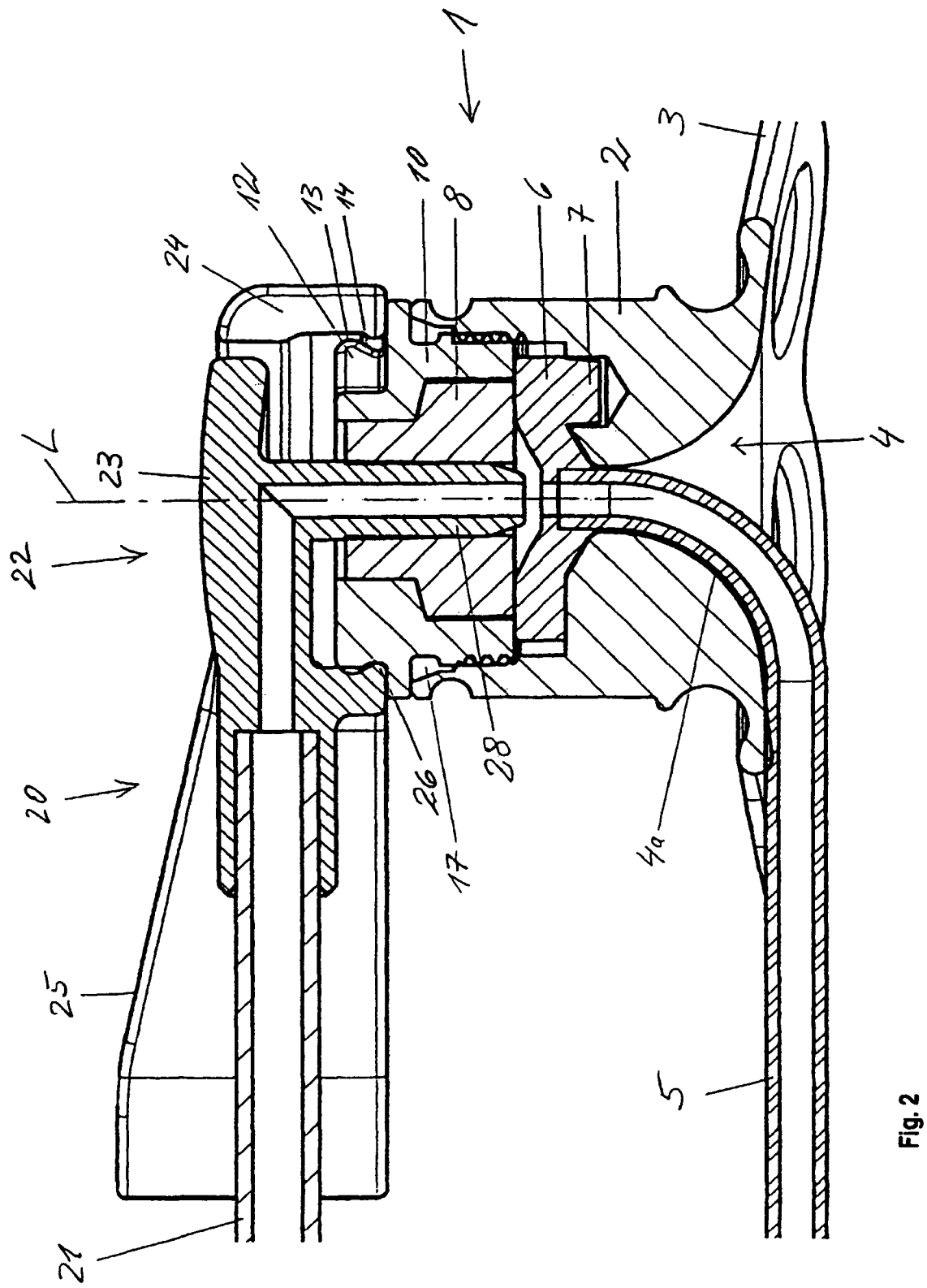
FIG. 2 depicts the port system of FIG. 1 when connected, in longitudinal section.

FIG. 2 shows one embodiments of the port system when connected. The reference numeral 1 refers to the percutaneous port from the anchoring body 3 to the membrane casing 10. The percutaneous port 1 comprises the main casing 2, the anchoring body 3, the membrane casing 10, the membrane 8 and the O-ring 17. In the exemplary embodiment, the supporting body 6 is counted as part of the implantable or implanted first fluid guiding system, due to its fixed connection to the catheter 5. As may be seen from FIGS. 1 and 2, the supporting body 6 forms a centering element 7 and the main casing 2 forms a receptacle into which the centering element 7 protrudes when assembled, in order to position the supporting body 6, and in particular its passage opening, in the main casing 2 with respect to the longitudinal axis L, preferably—as in the example embodiment—in order to pre-set a direction for the curved connector piece. The centering element 7 secures the supporting body 6 against rotating about the longitudinal axis L. The supporting body 6 comprises a plurality of recesses on its rim, said recesses forming passages for a tool, in order to be able to grip the supporting body 6 in order to remove the implanted catheter 5 and pull it out of the main casing 2. A single recess would in principle also suffice.

Another feature of the port 1 is the formation of a generally or substantially continuously rounded guide 4a for the connector piece of the implanted fluid guiding system 5, 6. The guide 4a extends from the casing opening in the base of the main casing 2 to the lower, peripheral rim of the main casing 2 and serves to deflect the catheter 5 into the casing opening without producing kinks. Not only the guide 4a is formed on the underside of the main casing 2 but also an opening funnel 4 in which the curved connector piece of the catheter 5 is largely protected from pressure loads. The opening funnel 4 opens from the casing opening in the shape of a trumpet, as shown by way of example.

Figure 3:
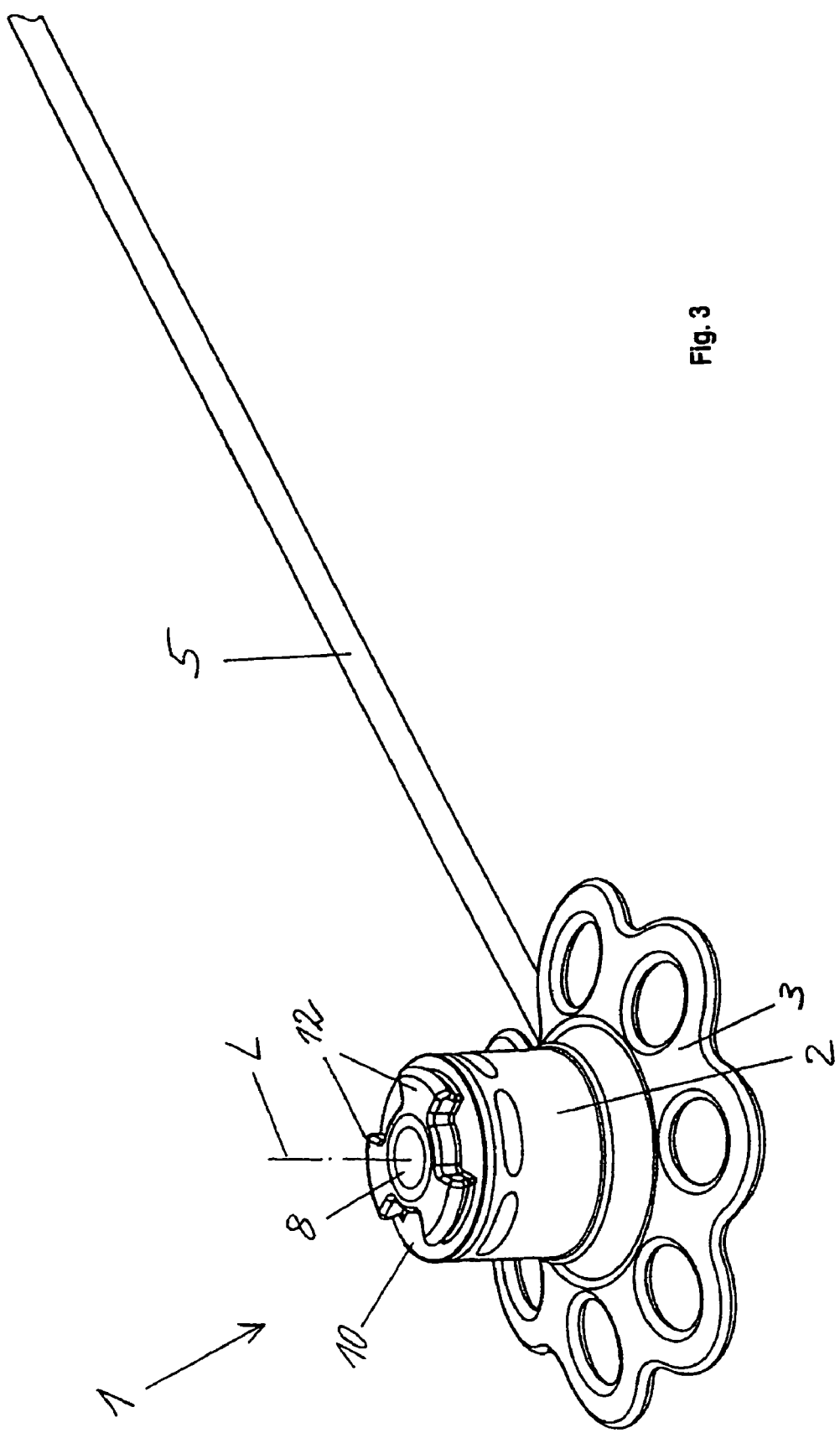
FIG. 3 depicts the part of the port system provided for implanting.

FIG. 3 shows the part of the port system provided for implanting again and on its own, in a perspective view.

Figure 4:
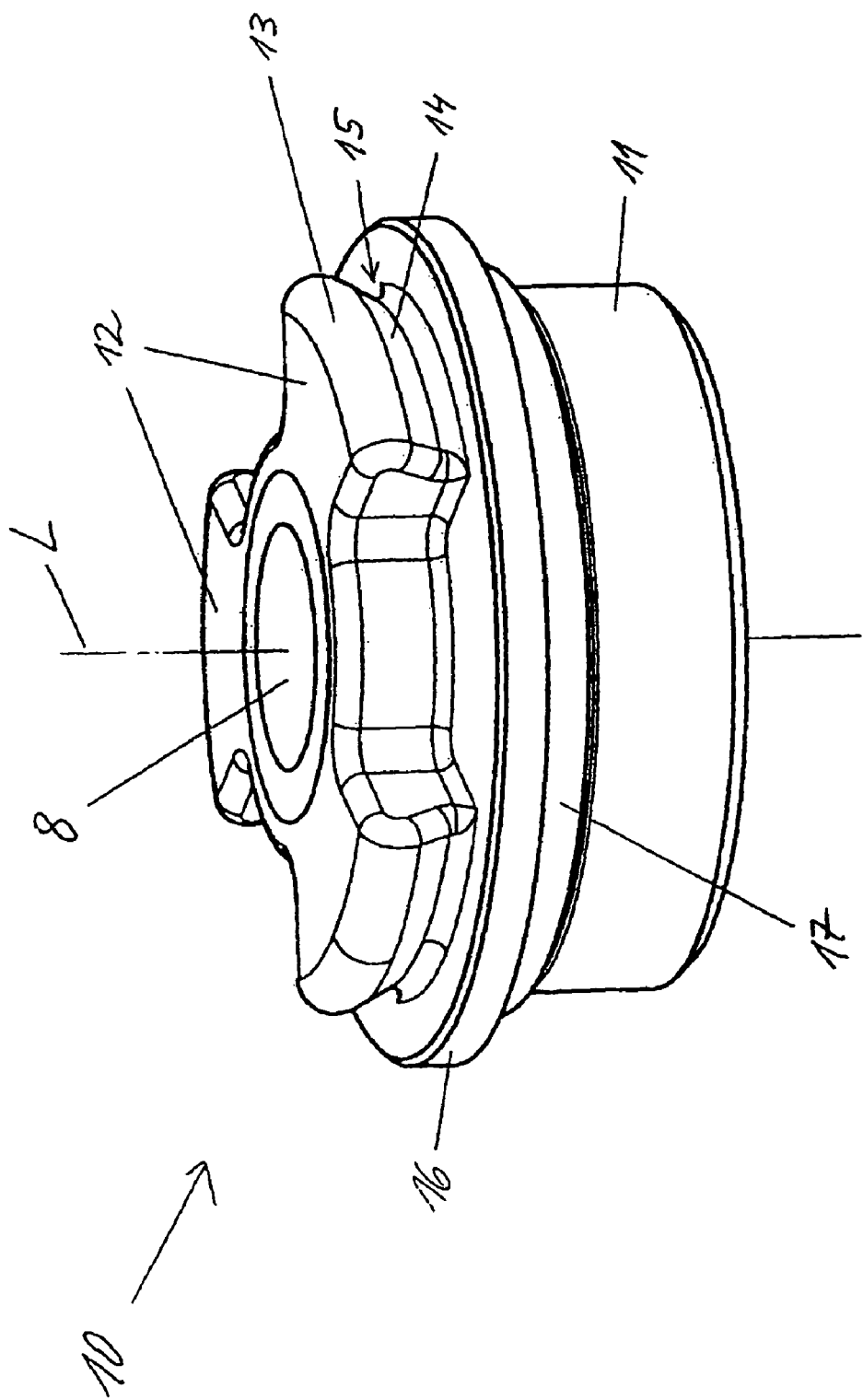
FIG. 4 depicts a membrane casing of the port system.

FIG. 4 shows the membrane casing 10 with the inserted membrane 8 and the attached O-ring 17, in a perspective view.

The membrane 8 is generally circular and cylindrical with an upper, smaller cross-section and a lower, larger cross-section. A central passage extends through the membrane 8 and is already sterilely sealed by the material elasticity of the membrane. When inserted, the membrane 8 is held in the membrane casing 10, pre-compressed by a certain radial tension. When assembled (FIGS. 2 and 3), the underside of the membrane casing 10 presses against the upper side of the supporting body 6 and presses it into its fit in the main casing 2. Simultaneously, the membrane 8 is also pressed via its underside against the supporting body 6, such that a sterile seal is formed encircling the central passage opening of the supporting body 6. The supporting body 6 slopes slightly from its rim towards its central passage opening. The passage opening of the supporting body 6 is hermetically sealed by the membrane 8.

The membrane casing 10 exhibits a two-stage inner cross-section along the longitudinal axis L, adapted to the shape of the membrane 8. On the outer circumference of the wider casing section, the lower casing section when assembled, an outer thread 11 is formed which serves to screw onto an inner thread of the main casing 2. The lower casing section of the membrane casing 10 is flared outwards, like a flange, by a stay 16. The O-ring 17 is accommodated in the inner edge region between the lower casing section and the stay 16 and when connected (FIG. 2) forms a seal between the membrane casing 10 and the main casing 2.

The membrane casing 10 forms three first connecting elements 12 on its upper side, which in the exemplary embodiment protrudes freely beyond the main casing 2. Each of the connecting elements 12 forms a radial protrusion 13 with a rear (as viewed from the upper side) collar 14 on the upper side of its radially outer rim. Each of the protrusions 13 taper via their collar 14 radially inwards. such that a constriction 15 arises in each case behind the protrusions 13 (as viewed from the upper side). In the longitudinal section of the membrane casing 10, each of the first connecting elements 12 forms, from the upper side, a protrusion 13 which initially curves radially outwards like a bulge and then curves radially back inwards and narrows again over the linear collars 14 radially inwards to the constriction 15. Each of the protrusions 13 forms a latching protrusion and each of the collars 14 forms a latching collar for a latching connection to the connecting head 22 (FIG. 2).

The first connecting elements 12 for latching elements which are generally non-flexible in their own right and also generally non-flexible relative to the membrane casing 10. Due to the generally rigid connection between the main casing 2 and the membrane casing 10, they are also generally non-flexible relative to the main casing 2.

Recesses are provided between the connecting elements 12, as viewed in the circumferential direction about the longitudinal axis L. The side walls of these recesses, formed by the connecting elements 12 and pointing towards each other, form rotational stoppers for a tool for establishing and releasing the rotational connection to the main casing 2. The connecting elements 12, pointing away from the longitudinal axis L like arms, thus form an assembly aid in a double function. The latching protrusions 13, the latching collars 14 and the constrictions 15 are formed by circular arcs about the longitudinal axis L. The recesses have no function with respect to connecting. With respect to the connecting function, the latching protrusions 13, the latching collars 14 and the constrictions 15 could just as easily encircle the longitudinal axis L, each in a closed circle. The circularity has the advantage that in the latching engagement of the first connecting elements 12 and the second connecting elements 24, the connecting head 22 can be rotated about the longitudinal axis L relative to the membrane casing 10. Due to this rotational capacity, shearing forces between the connecting head 22 and the percutaneous port 1 can be largely prevented.

The connecting head 22 is shown individually in FIG. 5 and when connected in FIG. 2, in each case in a longitudinal section. In addition, with respect to the connecting head 22, reference is also made to the top view onto its underside in FIG. 6 and to the top view onto its upper side in FIG. 7.

The connecting head is formed by a base body 23, a connecting cannula 28, the two second connecting elements 24 and the two grip elements 25. The connecting head 22 is moulded as a one-piece body comprising these functional components, in some preferred embodiments as an injection-moulded plastic body. A continuous fluid channel runs through the base body 23 from a rear connector region to the free tip of the connecting cannula 28. When connected, the longitudinal axis L of the connecting cannula 28 also forms the longitudinal axis of the port casing. The connecting cannula 28 and the outlet region of the implanted or implantable fluid guiding system in the percutaneous port 1 are thus flush when connected. The flow cross-section formed by the connecting cannula 28 is simply linearly extended in the outlet region of the fluid guiding system. Due to the flush arrangement and the unity of the flow cross-sections, a particularly low-resistance flow is obtained.

The two second connecting elements 24 are guided in an arc about the longitudinal axis L from a common root region to their front ends, between which a narrow, free gap remains. The base body 23 forms the root or connecting region of the two second connecting elements 24. Each of the connecting elements 24 is extended backwards beyond this root region to one of the grip elements 25. In this way, a pair of splaying pincers is obtained. The connecting elements 24 form the pincer jowls and the grip elements form the pincer arms of said pair of pincers. As can best be seen in the top views in FIGS. 6 and 7, the connecting head 22 exhibits a symmetrical shape with respect to a longitudinal plane which includes the longitudinal axis L and extends lengthways through the rear connector region and through the free gap between the front ends of the connecting elements 24.

On the underside on their inner surface area, the connecting elements 24 form a latching projection 26, pointing radially inwards, which in the latching engagement pre-latches behind the latching protrusions 13 of the first connecting elements 12 and presses against the latching collars 14 with an elasticity force, as shown in FIG. 2. The elasticity force acting in the latching engagement is generated in the root region of the base body 23 of the connecting head 22, namely by splaying the second connecting elements 24 radially outwards against the restoring force due to the material elasticity in the root region of the connecting head 22. The restoring elasticity force causes the two second connecting elements 24 to press against the first connecting elements 12 in the latching engagement with a pressing force directed radially inwards with respect to the longitudinal axis L. Due to the conical shape of the latching collars 14 and/or a corresponding counter shape of the latching projection 26, considerable axial tensile forces can be transferred in the latching engagement between the first connecting elements 12 and the second connecting elements 24, such that the latching engagement can be reliably prevented from being unintentionally released.

In the exemplary embodiment, the latching projection 26 extends, starting from the free ends of the two second connecting elements 24 which point towards each other, almost 360° about the longitudinal axis L without interruption. In principle, however, this is not necessary. In some embodiments, forming the latching projection continuously, however, is advantageous for the stability of the latching engagement and the free rotational capacity of the connecting head 22 relative to the percutaneous port 1.

When connected, the underside of the second connecting elements 24 contacts an upper side of the stay 16 of the membrane casing 10. Due to the elastic pressing contact with the latching collar 14 on the one hand and the contact with the upper side of the stay 16 on the other, a fastening engagement between the connecting elements 12 and 24 is obtained which prevents the connecting elements 12 and 24, and therefore the percutaneous port 1 and the connecting head 22, from moving relative to each other in the axial direction. In the exemplary embodiment, the percutaneous port 1 and the connecting head 22 have contact only via their connecting elements 12 and 24.

It would however also be possible, using the same connecting elements 12 and 24, the press the underside of the base body 23 directly onto the upper side of the percutaneous port 1. In the exemplary embodiment, however, a free space remains between the underside of the base body 23 and the upper side of the percutaneous port 1, through which only the connecting cannula 28 protrudes.

The grip elements 25 are moulded onto the root region of the connecting head 22 such that a movement of the grip elements 25 towards each other results in a radial splaying movement of the second connecting elements 24. The grip elements 25 are therefore helpful for releasing the latching engagement.

The pinching clamp 30 shown in FIG. 1 can advantageously form a securing means, by being pushed between the grip elements 25 on the external catheter 21 and in this position locking the grip elements 25 such that the latching engagement cannot be inadvertently released.

In the following, the port system is described by way of an exemplary procedure for an implantation in the human body:

Firstly, the catheter 5—sufficiently long for all practical applications—is cut to a length in accordance with the specific use or application. Then it is pulled through the casing opening of the underside of the main casing 2 and implanted by the operator. The supporting body 6 is moved into the main casing 2 to the position defined by the centering element 7, and the membrane casing 10 with the membrane 8 inserted into it is screwed into the main casing 2 until it presses against the supporting body and hermetically seals its outlet for the implanted catheter 5 all round, forming a hollow space.

In order to implant the port 1 under the skin, the operator scores the skin in the region of the location for inserting the catheter 5 and forms a skin pocket. The anchoring body 3 is pushed into the skin pocket, under the skin. At this point, directly before insertion, the anchoring body 3 is situated under the skin and the main casing 2 protruding up from the anchoring body 3 is situated partially above the skin. In the course of time, however, the main casing 2 grows in. In order to prevent inflammations, a germ barrier is formed on the outer side of the main casing 2 in the form of a circumferential constriction in the foot region. This germ barrier is intended to make it more difficult for external inflammatory germs to penetrate into the subcutaneous tissue. A skin stopper in the form of a circumferential protrusion on the main casing 2 caps the germ barrier. The skin stopper is intended on the one hand to restrict the ingrowth of the epidermis and on the other, if it is necessary to clean the wound, to prevent foreign bodies from penetrating into the subcutaneous tissue. Once grown in, only a small upper part of the main casing 2 is still visible from without, protruding above the surface of the skin. The body access thus formed is also sealed sterilely from the outside by the membrane 8.

In order to guide infusion fluid into the body via the percutaneous port 1 and the connected, implanted catheter 5 or to remove body fluid in the reverse direction, the external catheter 21 is connected fluidically and mechanically to the percutaneous port 1 with the aid of the connected catheter head 22. The connection is very simply established by inserting the connecting cannula 28, which protrudes beyond the connecting elements 24 on the underside, into the passage of the membrane 8 along the longitudinal axis L and is guided through as far as the position shown in FIG. 2. The penetrating connecting cannula 28 compresses the membrane 8 into indentations in the surface area of the membrane casing 10. Axially directly above the membrane 8, another equalisation space is created. The membrane 8 surrounds the connecting cannula 28 gas-tight on all sides during penetration and when connected.

In the course of the connecting movement, during which the connecting cannula 28 is also guided through the membrane 8, the latching projection 26 of the connecting jowls 24 comes into contact with the roundly sloping upper side of the latching protrusions 13. By gently pressing the connecting head 22 axially against the upper side of the latching protrusions 13, the two connecting jowls 24 are elastically splayed about their splaying axis or possibly also each about a splaying axis of its own. Once the latching projection 26 has slid over the latching protrusions 13, the two connecting jowls 24 move radially back inwards against the respectively facing latching collar 14 due to the restoring elasticity force.

The connecting elements 12 and the connecting jowls 24 are formed such that the connecting jowls 24 are not completely relieved in the latching engagement but rather press with a remaining elasticity residual force against the first connecting elements 12. In this way, a positive-lock and frictional-lock connection between the percutaneous port 1 and the connecting head 22 is obtained by the latching engagement. Due to the pressing force which acts between the connecting head 22 and the port casing via their connecting elements 12 and 24, the connecting head 22 and the port casing are fixed relative to each other, such that the connecting cannula 28 cannot be moved relative to the membrane 8 by the external tensile forces and tilting moments to be expected in practice. External pressure forces are absorbed by the contact between the second connecting elements 24 and the stay 16 of the port casing which exists in the latching engagement.

Embodiments of the present invention, including preferred embodiments, have been presented for the purpose of illustration and description. They are not intended to be exhaustive or to limit the invention to the precise forms disclosed. The scope of the invention should be determined by the appended claims when interpreted in accordance with the breadth they are fairly, legally, and equitably entitled.

The invention claimed is:

1. A port system, comprising:
an implantable first fluid guiding system comprising a disc-shaped supporting body;
an external second fluid guiding system with a connecting head at one end, the connecting head comprising a connecting cannula and two connecting jowls arranged transverse to the connecting cannula, the connecting jowls forming a latching projection formed of a curved arc of greater than 180°, the latching projection pointing radially inwardly to an underside of the connecting head, wherein the connecting jowls are each coupled to a grip element, the grip elements coupled to the connecting head such that a movement of the grip elements toward each other results in a radial splaying movement of the curved arc of the latching projection about an axis arranged perpendicular to the underside of the connecting head for facilitating connection of the connecting head; and
a percutaneously implantable port for establishing a fluid connection between said fluid guiding systems, said port comprising a port casing, which forms connecting elements protruding beyond the port casing and forming a radial protrusion configured to receive connecting head latching projection;
wherein said connecting head is fastened to said port casing by a releasable fastening engagement of said connecting elements and said connecting jowls upon the radial splaying movement of the connecting jowls.

2. The port system as set forth in claim 1, wherein the connecting elements and connecting jowls are elastically pressed onto each other in said fastening engagement with a pressing force.

3. The port system as set forth in claim 2, wherein the connecting elements and connecting jowls are configured such that they press against each other in the fastening engagement, with a first force component parallel to said pressing force and a second force component transverse to the pressing force.

4. The port system as set forth in claim 3, wherein the connecting elements and connecting jowls latch together in the fastening engagement in a positive-lock and frictional-lock.

5. The port system as set forth in claim 4, wherein one of the connecting elements forms a latching protrusion comprising a latching collar and the connecting jowls forms a latching projection which, in the fastening engagement, grips behind said latching protrusion and elastically presses against said latching collar.

6. The port system as set forth in claim 5, wherein the connecting element latching protrusion comprising the latching collar gradually tapers to a constriction.

7. The port system as set forth in claim 1, wherein the connecting head comprises a connecting cannula which, in the fastening engagement of the connecting elements, protrudes into the port casing and is freed from or at least relieved of external forces by the fastening engagement.

8. The port system as set forth in claim 1, wherein the grip elements form a pair of pincers.

9. The port system as set forth in claim 1, wherein the connecting elements are molded non-flexibly on the port casing.

10. The port system as set forth in claim 1, wherein the port casing comprises a main casing and a membrane casing, which serves to accommodate a sealing membrane, protrudes into the main casings and is releasably connected to the main casing, and wherein the connecting elements are formed by the membrane casing.

11. The port system as set forth in claim 1, wherein the connecting elements gradually flare to a latching protrusion on an upper side facing the connecting head and said latching protrusion encircles a longitudinal axis of the sleeve-shaped port casing and is then constricted in the longitudinal direction to form a latching collar for the second connecting element.

12. The port system as set forth in claim 11, wherein the latching protrusion and the latching collar encircle said longitudinal axis of the port casing in curved arc segments.

13. The port system as set forth in claim 1, wherein the port casing comprises a main casing and a membrane casing which serves to accommodate a membrane and can be screwed onto the main casing, and wherein a plurality of arm elements, which radially point away from a longitudinal axis of the port casing on an upper side of the port casing and serve as rotational stoppers for a tool, for establishing the rotational connection, each form connecting elements.

14. The port system as set forth in claim 1, wherein the connecting head comprises a connecting cannula and wherein the first fluid guiding system feeds in or into the port casing, flush with said connecting cannula, in order to avoid or at least minimize turbulence in the fluid at a transition between the connecting cannula and the first fluid guiding system.

15. The port system as set forth in claim 1, wherein the connecting head comprises a connecting cannula and said connecting cannula and at least one connector region of the first fluid guiding system, guided into the port casing, exhibit the same flow cross-section, in order to avoid or at least minimize turbulence in the fluid.

16. The port system as set forth in claim 1, wherein the port casing forms a curved guide on an underside, in order to deflect a catheter of the first fluid guiding system, attached to said guide, to the casing opening without producing kinks.

17. The port system as set forth in claim 16, wherein the port casing forms an opening funnel on its underside and said opening funnel expands from the casing opening out and protects a catheter of the first fluid guiding system from kinks.

18. The port system of claim 1, wherein the percutaneously implantable port comprises a port casing having a threaded surface;

and wherein the connecting device comprises an outer threaded surface configured to engage with the port casing threaded surface.

* * * * *